US010765445B2

(12) United States Patent
Farago

(10) Patent No.: US 10,765,445 B2
(45) Date of Patent: Sep. 8, 2020

(54) THROMBECTOMY CATHETER

(71) Applicant: BOSTON SCIENTIFIC SCIMED, INC., Maple Grove, MN (US)

(72) Inventor: Laszlo Trent Farago, Hudson, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 183 days.

(21) Appl. No.: 15/782,527

(22) Filed: Oct. 12, 2017

(65) Prior Publication Data

US 2018/0098782 A1    Apr. 12, 2018

Related U.S. Application Data

(60) Provisional application No. 62/407,246, filed on Oct. 12, 2016.

(51) Int. Cl.
| A61B 17/3203 | (2006.01) |
| A61M 25/00 | (2006.01) |
| A61B 17/22 | (2006.01) |
| A61B 17/00 | (2006.01) |
| A61M 25/10 | (2013.01) |

(52) U.S. Cl.
CPC ... *A61B 17/32037* (2013.01); *A61M 25/0071* (2013.01); *A61B 17/22032* (2013.01); *A61B 2017/00154* (2013.01); *A61M 2025/109* (2013.01)

(58) Field of Classification Search
CPC ... A61B 17/32037; A61B 2017/00154; A61M 25/0071
See application file for complete search history.

(56) References Cited

U.S. PATENT DOCUMENTS

| 5,370,609 A * | 12/1994 | Drasler ............ A61B 17/32037 |
| | | 604/22 |
| 5,766,194 A | 6/1998 | Smith |
| 6,423,027 B1 | 7/2002 | Gonon |
| 6,572,578 B1 | 6/2003 | Blanchard |

(Continued)

FOREIGN PATENT DOCUMENTS

| WO | 94/10917 A1 | 5/1994 |
| WO | 2012/135794 A1 | 10/2012 |

OTHER PUBLICATIONS

International Search Report and Written Opinion dated Jan. 17, 2018 for International Application No. PCT/US2017/056370.

*Primary Examiner* — Bradley J Osinski
(74) *Attorney, Agent, or Firm* — Seager, Tufte & Wickhem, LLP

(57) ABSTRACT

An example thrombectomy device is disclosed. The example thrombectomy catheter includes a catheter tube including a proximal portion, a distal portion and a lumen extending therein. The thrombectomy catheter also includes a high pressure tube extending through the catheter lumen from the catheter proximal portion toward the catheter distal portion, the high pressure tube having at least one jet orifice for directing at least one fluid jet through the catheter lumen. The thrombectomy catheter also includes an outflow orifice, an inflow orifice and a fluid pulse generator coupled to the proximal portion of the catheter tube, wherein the fluid pulse generator is configured to inject fluid though the thrombectomy catheter at a first frequency.

14 Claims, 13 Drawing Sheets

(56) References Cited

U.S. PATENT DOCUMENTS

| | | |
|---|---|---|
| 7,226,433 B2 | 6/2007 | Bonnette et al. |
| 8,998,843 B2 | 4/2015 | Bonnette et al. |
| 9,078,691 B2 | 7/2015 | Morris et al. |
| 2011/0152908 A1 | 6/2011 | Morris et al. |
| 2011/0301594 A1* | 12/2011 | Orion ................ A61B 18/1492 606/41 |
| 2014/0296896 A1 | 10/2014 | Kojima et al. |

* cited by examiner

THROMBECTOMY CATHETER

CROSS-REFERENCE TO RELATED APPLICATIONS

This application claims the benefit of priority under 35 U.S.C. § 119 to U.S. Provisional Application No. 62/407,246, filed Oct. 12, 2016, the entire disclosure of which is herein incorporated by reference.

TECHNICAL FIELD

The disclosure is directed to a thrombectomy catheter, and more particularly, relates to an enhanced cross stream mechanical thrombectomy catheter including a fluid pulse generator for delivering pulsed fluid through the catheter system. The intended use of embodiments of this disclosure are for the detachment and removal of unwanted tissues, such as thrombus, from within biological conduits.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example thrombectomy catheter includes a catheter tube including a proximal portion, a distal portion and a lumen extending therein. The thrombectomy catheter also includes a high pressure tube extending through the catheter lumen from the catheter proximal portion toward the catheter distal portion, the high pressure tube having at least one jet orifice for directing at least one fluid jet through the catheter lumen. The thrombectomy catheter also includes an outflow orifice, an inflow orifice and a fluid pulse generator coupled to the proximal portion of the catheter tube, wherein the fluid pulse generator is configured to inject fluid though the thrombectomy catheter at a first frequency.

Alternatively or additionally to any of the embodiments above, wherein the first frequency approximates a resonant frequency of a target site.

Alternatively or additionally to any of the embodiments above, wherein the fluid pulse generator is configured to inject fluid in a pulsatile flow.

Alternatively or additionally to any of the embodiments above, wherein the fluid pulse generator is configured to inject fluid at a second frequency different from the first frequency.

Alternatively or additionally to any of the embodiments above, wherein the first frequency is within 5% of the resonant frequency.

Alternatively or additionally to any of the embodiments above, wherein the first frequency is less than or equal to 30 MHz.

Alternatively or additionally to any of the embodiments above, wherein the first frequency is 23-27 MHz.

Alternatively or additionally to any of the embodiments above, wherein the fluid pulse generator includes a fluid inlet portion, a fluid outlet portion and a frequency modulating portion extending therebetween.

Alternatively or additionally to any of the embodiments above, wherein the frequency modulating portion includes a disruptor, and wherein the disruptor is intended to disrupt the flow of fluid through the fluid pulse generator.

Another example thrombectomy catheter includes:
a catheter tube including an inlet portion, an outlet portion and a lumen extending therein; and
a fluid pulse generator coupled to the inlet portion of the catheter tube;
wherein the fluid pulse generator is configured to inject fluid into the lumen of the catheter tube at a frequency less than or equal to 30 MHz.

Alternatively or additionally to any of the embodiments above, wherein the frequency approximates a resonant frequency of a target site.

Alternatively or additionally to any of the embodiments above, wherein the fluid pulse generator is configured to inject fluid in a pulsatile flow.

Alternatively or additionally to any of the embodiments above, wherein the fluid pulse generator is configured to inject fluid at a second frequency different from the first frequency.

Alternatively or additionally to any of the embodiments above, wherein the first frequency is 23-27 MHz.

Alternatively or additionally to any of the embodiments above, wherein the fluid pulse generator includes a fluid inlet portion, a fluid outlet portion and a frequency modulating portion extending therebetween.

Alternatively or additionally to any of the embodiments above, wherein the frequency modulating portion includes a disruptor, and wherein the disruptor is intended to disrupt the flow of fluid through the fluid pulse generator.

A method of treating a body lumen includes:
advancing a thrombectomy catheter to a target site, the thrombectomy catheter including:
  a catheter tube including a proximal portion, a distal portion and a lumen extending therein;
  a high pressure tube extending through the catheter lumen from the catheter proximal portion toward the catheter distal portion;
  a fluid jet emanator in communication with the high pressure tube, the fluid jet emanator having at least one jet orifice for directing at least one fluid jet from said fluid jet emanator through the catheter lumen;
  an outflow orifice located along a catheter perimeter of the catheter distal portion;
  an entrainment inflow orifice positioned along the catheter distal portion; and
  a fluid pulse generator coupled to the proximal portion of the catheter tube;
injecting fluid through the thrombectomy catheter in a pulsatile flow.

Alternatively or additionally to any of the embodiments above, wherein injecting fluid through the thrombectomy catheter in a pulsatile flow includes using the fluid pulse generator to inject the fluid at a first frequency, and wherein the first frequency approximates the resonant frequency of the target site.

Alternatively or additionally to any of the embodiments above, wherein using the fluid pulse generator to inject fluid at a first frequency, and wherein the first frequency is within 5% of the resonant frequency of the target tissue.

Alternatively or additionally to any of the embodiments above, wherein the first frequency is less than or equal to 30 MHz.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
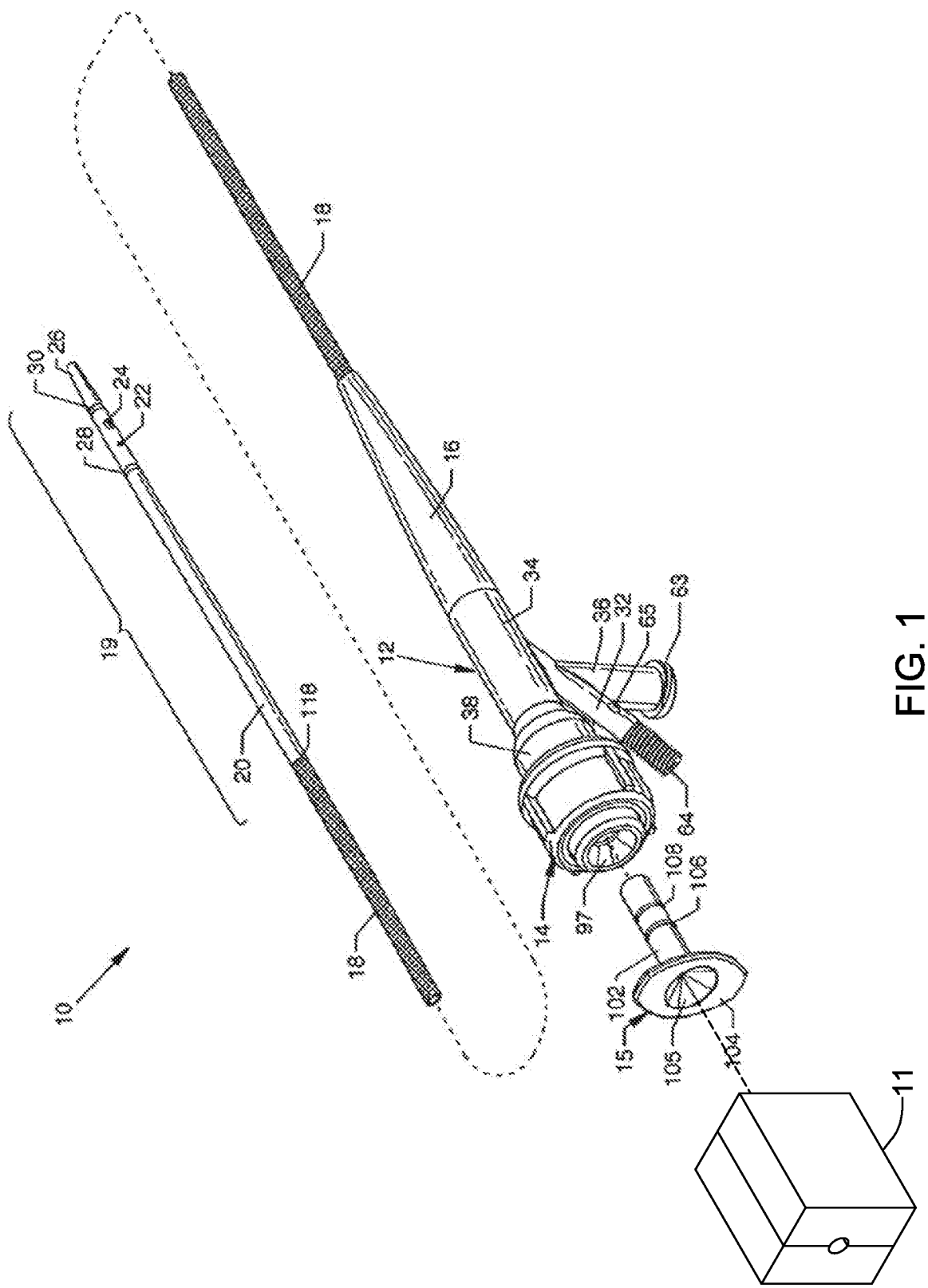
FIG. 1 is an isometric view of a thrombectomy catheter.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. These devices may be effective to remove acute thrombus, organized thrombus, or areas of large clot burden such as that seen in deep vein thrombosis (DVT). Further, in some instances thrombolytic therapy may be improved by introducing a specific amount of mechanical energy at a particular frequency (e.g., rate) which has been determined to increase the effectiveness in which thrombi may be disrupted and/or removed. For example, mechanical energy in the form of pulsed fluid flow (e.g., fluid injected at a specific frequency) may improve a thrombectomy system's ability to efficiently disrupt and/or remove targeted thrombi. Therefore, it may be desirable to provide a thrombectomy system including a fluid pulse generator to be used in combination with the thrombectomy catheter.

FIG. 1 is an isometric view of an enhanced cross stream mechanical thrombectomy catheter 10 with a backloading manifold 12. Externally visible major components of an embodiment of the present disclosure may include a centrally located backloading manifold 12, a flexible and tapered strain relief 16 connected to and extending from the backloading manifold 12, a catheter tube extending from a proximal portion to a distal portion and composed of a braided catheter tube 18 connected to the backloading manifold 12 and extending through the tapered and flexible strain relief 16 and a smooth catheter tube assembly 19 having a smooth catheter tube 20 connected to and extending distally from the braided catheter tube 18. The components of the smooth catheter tube assembly 19 are depicted fully in FIGS. 2 and 3. In some cases, the braided catheter tube may be formed of a flexible or semi-flexible material, such as but not limited to polyimide or other such suitable composition. It is contemplated that the smooth catheter tube 20 may be formed of a plastic composition, although this is not required. In some cases, the catheter tube 18 is formed as a braided construction for strength, as shown, but it can be effectively formed in other ways: for example, by using reinforcing components such as fibers, wound strands, rings, wraps, or combinations thereof. Also shown is the junction 118 between the smooth catheter tube 20 and the braided catheter tube 18, such junction being suitably effected to provide for a smooth and continuous coupling of the smooth catheter tube 20 and the braided catheter tube 18.

An outflow orifice 22 and an entrainment inflow orifice 24 may be located in longitudinal alignment along an imaginary line at the distal portion of the smooth catheter tube 20 near a flexible tapered tip 26 located distally at the end of the smooth catheter tube 20. For illustration purposes, the outflow orifice 22 and the inflow orifice 24, which extend through the smooth catheter tube 20, are shown on the side of the smooth catheter tube 20, but can be located along any imaginary line extending longitudinally along a distal surface of the smooth catheter tube 20, such as is shown in FIGS. 3, 7, 10, and 11. In some embodiments, the thrombectomy catheter 10 may further include a radiopaque marker band 28 located on the smooth catheter tube 20 in close proximity to and proximal to the outflow orifice 22, a radiopaque marker band 30 located on the smooth catheter tube 20 in close proximity to and distal to the inflow orifice 24.

The backloading manifold 12 may further include a central body 34 having a proximally located cavity body 38. The central body 34 may be coupled to a proximal end of the strain relief 16. A hemostatic nut 14 may be threadingly secured to the backloading manifold 12. The hemostatic nut 14 may include a beveled surface entrance configured to receive an introducer 15. The introducer 15 may include a centrally located shaft 102 with a beveled surface entrance 105, an actuating handle 104, and rings 106 and 108 about the shaft 102.

Other externally visible major components may include, a high pressure connection branch 32 extending from the central body 34 of the backloading manifold 12, an exhaust branch 36 extending from the junction of the central body 34 of the backloading manifold 12 and the high pressure connection branch 32, and a high pressure connector 64 engaging with and extending from the high pressure connection branch 32 of the backloading manifold 12. An orifice 65 located in the high pressure connection branch 32 may allow for the introduction of an adhesive to secure the high pressure connector 64 in the high pressure connection branch 32. The exhaust branch 36 may have a threaded surface 63 at its end for attaching to suction apparatus.

Additionally, FIG. 1 illustrates pulse generator 11 coupled to a proximal portion of thrombectomy catheter 10. For example, pulse generator 11 may be coupled to a portion of backloading manifold 12 and/or introducer 15. In particular, pulse generator 11 may be coupled to high pressure connector 64 and/or high pressure connection branch 32.

In some instances, pulse generator 11 may be designed to introduce (e.g., inject) fluid into thrombectomy catheter 10. For purposes of the discussion herein, pulse generator 11 may also be referred to as fluid pulse generator 11. For example, fluid pulse generator 11 may be designed to introduce fluid high pressure connector 64 and/or the high pressure connection branch 32. Fluid injected into high pressure connector 64 and/or high pressure connection branch 32 may further be introduced into the various components of the thrombectomy catheter systems described herein.

For purposes of this discussion, pulse generator 11 may generally be described as a component designed to inject or introduce fluid into catheter 10 in a pulsatile manner. It can be appreciated that the term "pulsatile fluid flow" as used herein may define that a fluid passed through a particular component and/or via an example methodology moves at a particular power intensity and at a particular frequency through catheter system 10. For purposes of discussion herein, the power intensity (e.g., power) of fluid flowing through catheter system 10 may be described as the amount of energy each one of the pulses may contain. Further, for purposes of discussion herein, the frequency may be described as the rate at which the pulses may pass through catheter system 10. In other words, pulse generator 11 may be designed to receive fluid flowing at a constant flowrate and a particular power from an external fluid source, disrupt (e.g., convert) that constant fluid flow into a pulsed fluid flow and eject that fluid such that exits pulse generator 11 in a pulsatile manner (e.g., as a pulsed fluid flow defined by a particular frequency at a given power).

As stated above, the disruption and/or elimination of a target thrombi (e.g., thrombosis located in a target vessel) may be improved when thrombectomy catheter 10 is utilized to pulse fluid at a frequency and power that approximates a "resonant" (e.g., natural) frequency of the thrombolytic material being targeted. For purposes of discussion herein, the resonant frequency of a target site (e.g., thrombus, plaque, etc.) may be defined as the particular frequency (at a particular power) where the greatest rate of thrombus disruption or elimination of a target site (e.g., thrombus, plaque) occurs. Traditional applications of a thrombectomy catheter may include injecting fluid flowing through the thrombectomy system in a constant stream or fluid flow (e.g., no pulsatile flow). However, thrombectomy systems disclosed herein may enhance the effectiveness of the fluid disrupting the target site by pulsing the fluid at a frequency and/or power which approximates and/or matches the resonant frequency of the target site (e.g., the resonant frequency of the thrombus, plaque, etc. being targeted).

In some instances, fluid pulse generator 11 may be able to introduce fluid into thrombectomy system 10 at more than one frequency and/or power. For example, in some instances fluid pulse generator 11 may introduce fluid at a variety of frequencies and/or powers which target the resonant frequency of a particular thrombus, plaque, etc. For example, in some instances pulse generator 11 may inject fluid through thrombectomy system 10 at frequencies less than or equal to 30 MHz, or at frequencies from 20 MHz to 30 MHz, or at frequencies from 23 MHz to 27 MHz, or at a frequency of about 25 MHz.

Figure 2:
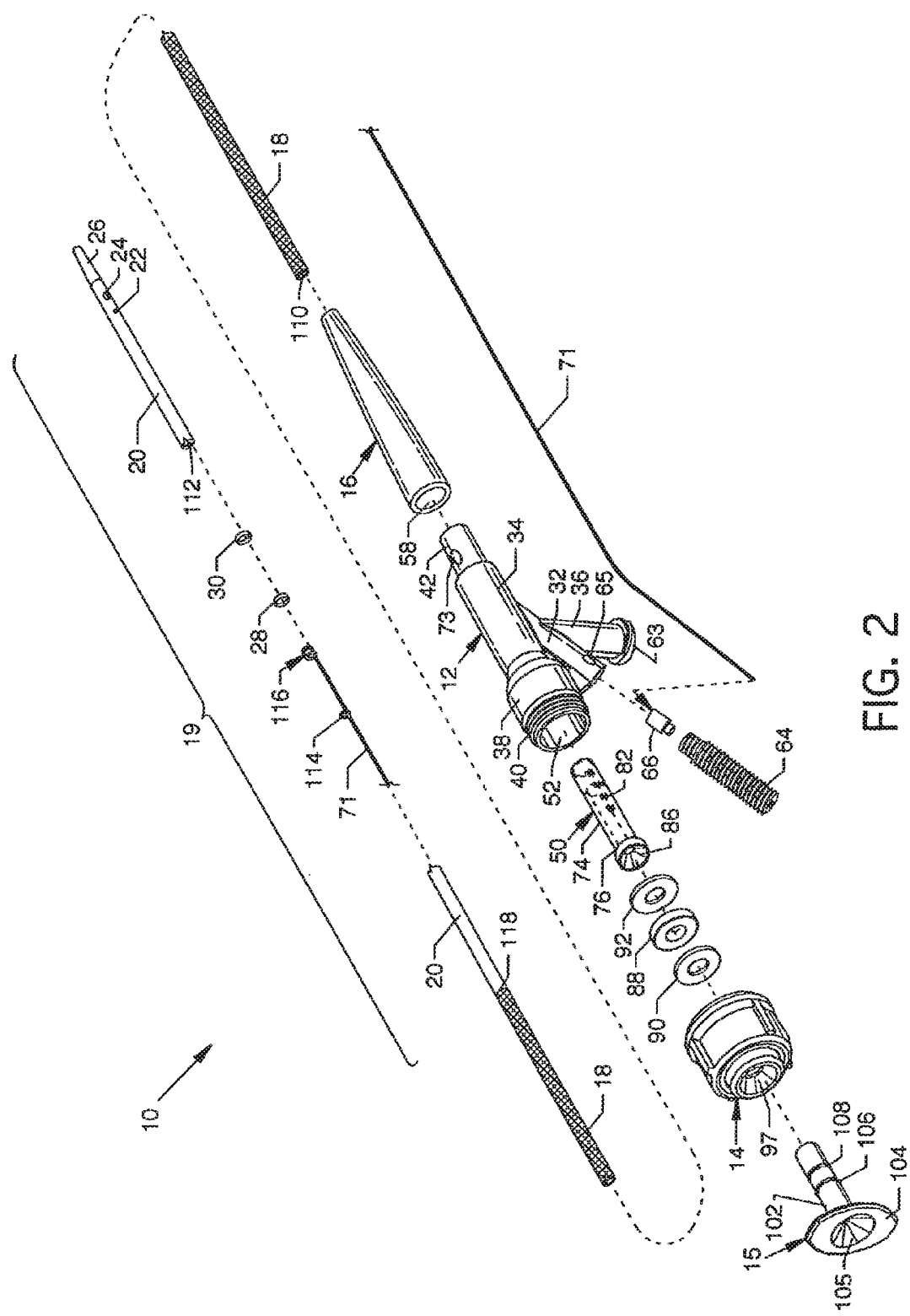
FIG. 2 is an isometric exploded view of the thrombectomy catheter.
Figure 3:
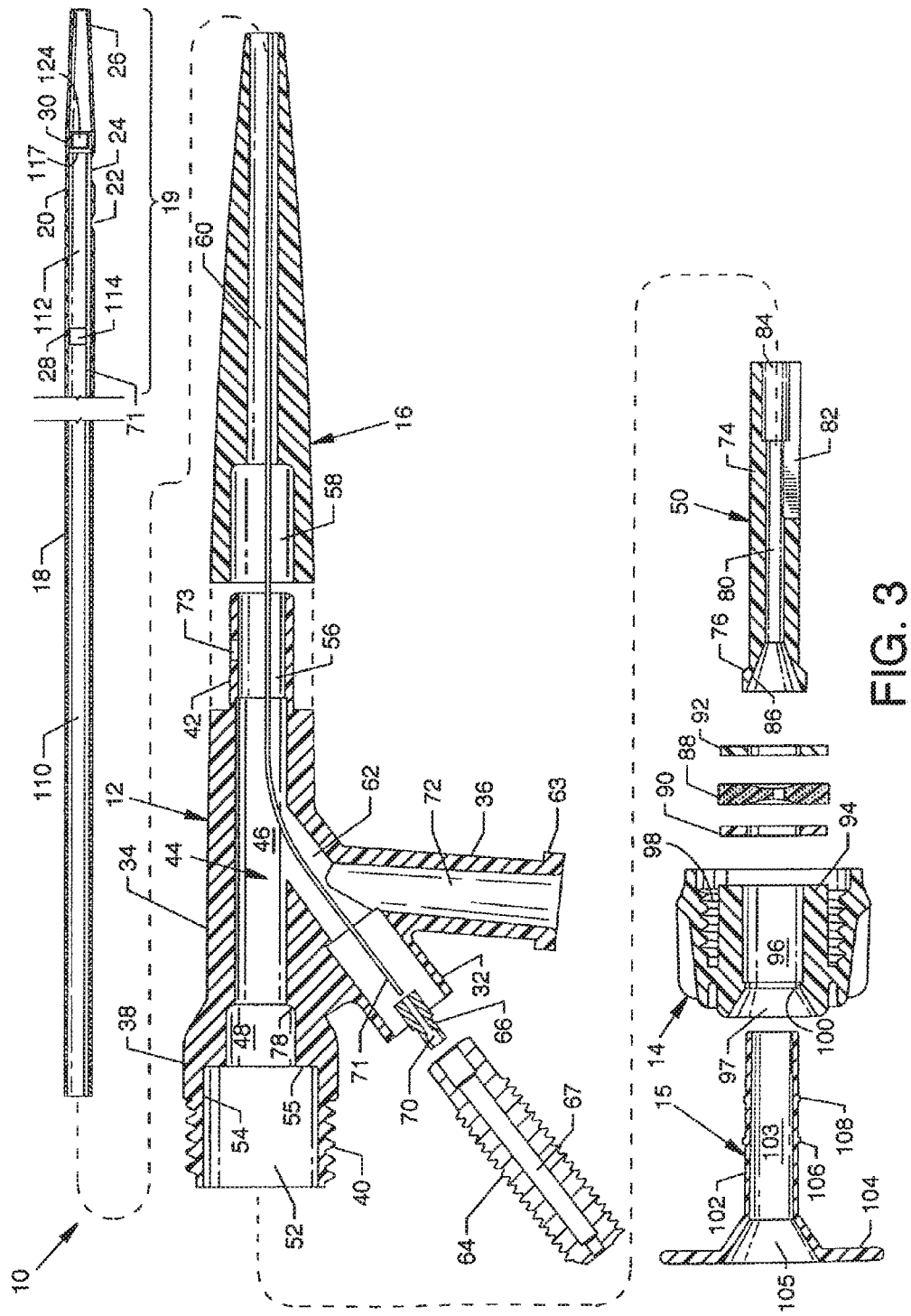
FIG. 3 is an exploded cross section side view of the components of the thrombectomy catheter.

FIG. 2 is an isometric exploded view of the enhanced cross stream mechanical thrombectomy catheter with backloading manifold 12, and FIG. 3 is an exploded cross section side view of the components of the enhanced cross stream mechanical thrombectomy catheter with a backloading manifold 12.

Figure 5:
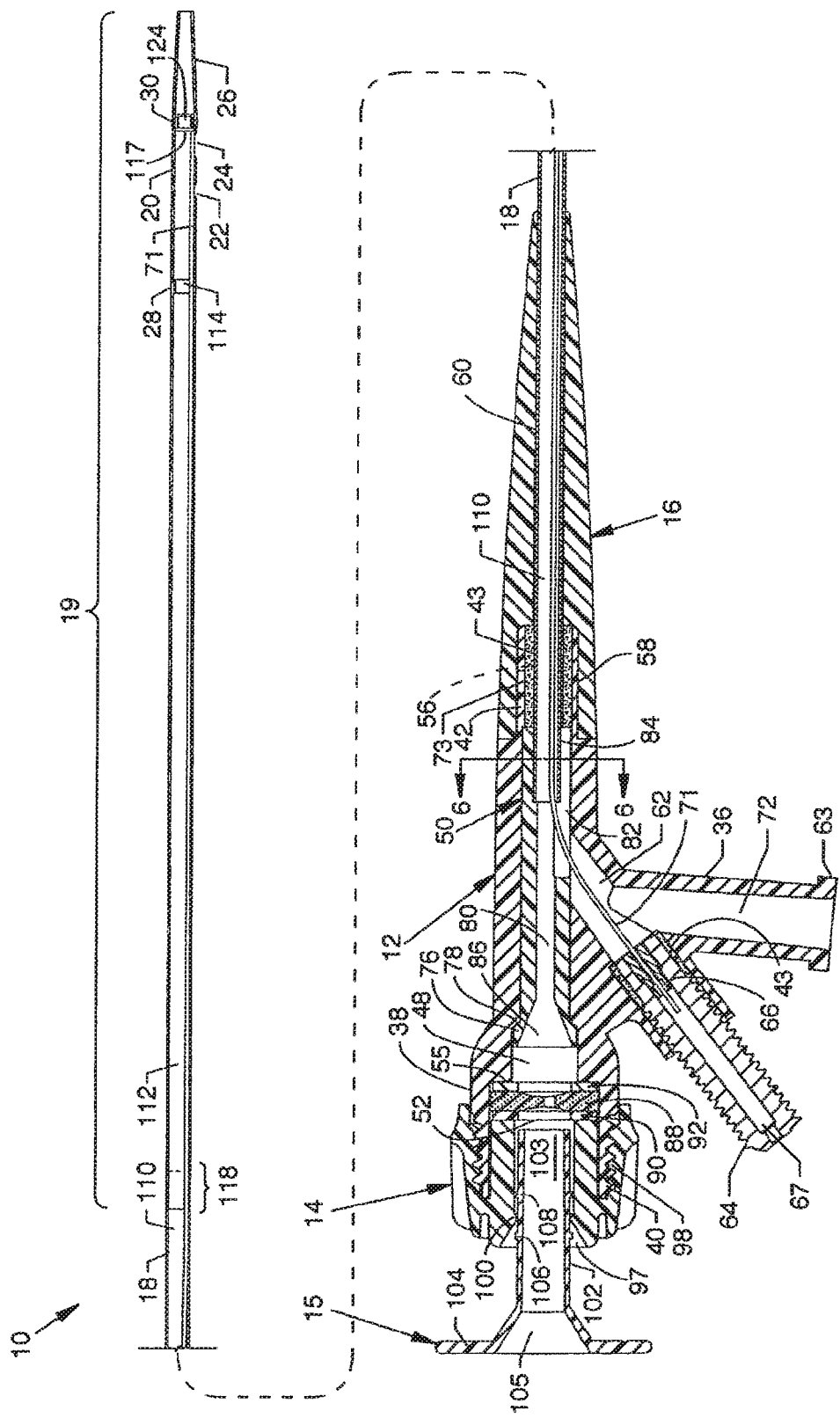
FIG. 5 is a cross section view of the assembled elements of FIG. 3.

As described herein, the backloading manifold 12 may include the central body 34 which may be tubular and have on one end a proximally located cavity body 38 including an externally located threaded surface 40 and on the other end a distally located tubular manifold extension 42, including an orifice 73 which may be utilized to introduce adhesive 43 (as shown in FIG. 5) to secure the proximal end of the braided catheter tube 18 to the distal manifold cavity 56. A multi-radius insert cavity 44 is continuously co-located within the central body 34 and a portion of the adjacent cavity body 38. The multi-radius insert cavity 44 is comprised of an elongated distal insert cavity portion 46 located coaxially within the central body 34 adjacent to and connecting to a proximal insert cavity portion 48 located coaxial to the cavity body 38 in continuous fashion. The insert cavity 44 accommodates an insert 50. The entire insert 50 is accommodated by the insert cavity 44 where the distal insert cavity portion 46 and the proximal insert cavity portion 48 fittingly accommodate separate geometric configurations of the insert 50.

A proximal manifold cavity 52 is located coaxially within the cavity body 38 and is continuous with and proximal to the proximal insert cavity portion 48 and an annular cavity wall 54 and an annular and planar surface 55 located between the annular cavity wall 54 and the proximal insert cavity portion 48. The manifold extension 42 extending distally from the distal end of the backloading manifold 12 includes an inwardly located distal manifold cavity 56 for passage of the proximal end of the braided catheter tube 18. The exterior of the manifold extension 42 accommodates the strain relief 16. The strain relief 16 is of flexible construction and includes a proximally located strain relief mounting cavity 58 connected to a passageway 60 both of which extend along the longitudinal axis of the strain relief 16. The strain relief mounting cavity 58 accommodates the manifold extension 42, which can be appropriately secured therein, such as by adhesive or mechanical interference.

The high pressure connection branch 32 includes a high pressure connection branch passageway 62 intersecting and communicating with the distal insert cavity portion 46 of the insert cavity 44, as well as offering accommodation of the threaded high pressure connector 64. The threaded high pressure connector 64 may be configured to be operatively coupled to a fluid source positioned near the proximal portion of the catheter 18, 20 to provide communication between the fluid source and the high pressure tube 71. In some cases, the fluid source may be directly coupled to the high pressure connector 64 and in other cases the fluid source may be indirectly coupled to the high pressure connector 64. A ferrule 66 having a central bore 70 is accommodated by the lumen 67 of the high pressure connector 64. One end of a high pressure tube 71 is accommodated by and sealingly secured to the central bore 70 of the ferrule 66, such as by a weldment or mechanical interference. An exhaust branch passageway 72 central to the exhaust branch 36 communicates with the high pressure connection branch passageway 62 and with the distal insert cavity portion 46 of the insert cavity 44. The exhaust branch 36 has a threaded surface 63 at its end for attaching to a suction apparatus. As also shown in the isometric view of FIG. 4, the insert 50 includes a tubular main body 74 having a proximally located shoulder 76 which can be tapered or of other suitable geometric configuration. The shoulder 76 engages an annular transition stop surface 78 (FIG. 3) between the proximal insert cavity portion 48 and the distal insert cavity portion 46. One end of a central passageway 80 truncatingly intersects an elongated slot 82; and such central passageway also intersects a bore 84 which is also truncated by intersecting the elongated slot 82, e.g., the central passageway 80 adjoins bore 84 and each is truncated by intersection with the elongated slot 82. The elongated slot 82 extends through the main body 74 to intersect and align to a portion of the longitudinal axis of the insert 50. The elongated slot 82 accommodates passage of the high pressure tube 71, as shown in FIG. 5. The central passageway 80 has a proximally located beveled surface entrance 86 resembling a cone. The beveled surface entrance 86 is utilized for guidance and alignment for backloading of a guidewire through the backloading manifold 12, as described herein.

Beneficial to an embodiment of the present disclosure is the use of a self-sealing hemostatic valve 88, flanking washers 90 and 92, and an introducer 15 which are related to a patent application entitled "Thrombectomy Catheter Device Having a Self-Sealing Hemostatic Valve," U.S. Pat. No. 7,226,433, which is herein incorporated by reference. The self-sealing hemostatic valve 88, which is slightly oversized with respect to the proximal manifold cavity 52, and the washers 90 and 92 are aligned in and housed in the proximal manifold cavity 52 at one end of the backloading manifold 12. The hemostatic nut 14 includes a centrally located cylindrical boss 94, a central passageway 96 having a beveled surface entrance 97 extending through and in part forming the cylindrical boss 94, and internal threads 98. The internal threads 98 of the hemostatic nut 14 can be made to engage the threaded surface 40 of the backloading manifold 12, whereby the cylindrical boss 94 is brought to bear against the washer 90 to resultantly bring pressure to bear as required against the self-sealing hemostatic valve 88 and washer 92. The washers 90 and 92 and the self-sealing hemostatic valve 88 are captured in the proximal manifold cavity 52 by threaded engagement of the hemostatic nut 14 to the cavity body 38 of the backloading manifold 12. Also included in the hemostatic nut 14 is an annular lip 100 which can be utilized for snap engagement of particular styles or types of introducers, as required, such as introducer 15 provided to aid in accommodation of a guidewire in either direction and to provide for venting for the interior of the backloading manifold 12. The introducer 15 includes a centrally located shaft 102 with a central passageway 103 having a beveled surface entrance 105, an actuating handle 104, and rings 106 and 108 about the shaft 102.

Also shown in FIG. 3 is a catheter lumen 110 central to the braided catheter tube 18 which joiningly connects to and communicates with a lumen 112 central to the smooth catheter tube 20 to form a lumen extending between the proximal portion and the distal portion of the catheter tube. The high pressure tube 71 may extend through the lumen 110 of the braided catheter tube 18 and the lumen 112 of the smooth catheter tube 20. A circular support ring 114 is suitably attached to the high pressure tube 71, such as by a weldment, and is located within the smooth catheter tube 20 in supporting alignment with the radiopaque marker band 28. A fluid jet emanator 116 including terminated loop 117 at and in fluid communication with the distal end of the high pressure tube 71 and a circular support ring 124 is located distal of the inflow orifice 24 within the distal end of the smooth catheter tube 20 in alignment with the radiopaque marker band 30, as described in detail with respect to FIG. 10. The circular support rings 114 and 124 together with the respective associated radiopaque marker bands 28 and 30 constitute means for retaining the high pressure tube 71 in alignment with the catheter tube composed of braided catheter tube 18 and the smooth catheter tube 20.

Figure 4:
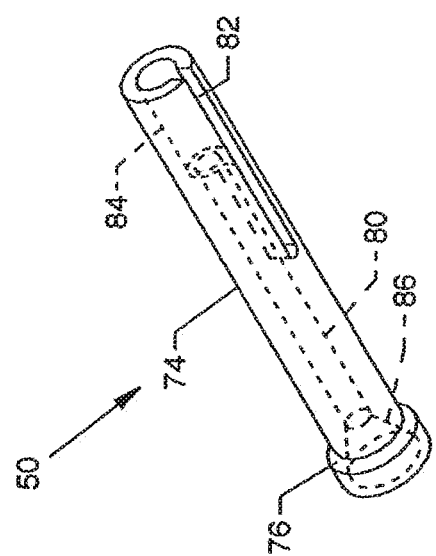
FIG. 4 is an isometric view of the insert showing an elongated slot extending through the main body.

FIG. 4 is an isometric view of the insert 50 showing the elongated slot 82 extending through the main body 74 in intersection with the central passageway 80 and the bore 84. The elongated slot 82 is beneficial for accommodation of the high pressure tube 71, as well as for communication between the combined lumens 110 and 112 of the braided catheter tube 18 and the smooth catheter tube 20, respectively, and the high pressure connection branch passageway 62 and the exhaust branch passageway 72, as shown in FIG. 5.

FIG. 5 is a cross section view of the assembled elements of FIG. 3. Particularly shown is the relationship of the high pressure tube 71, the insert 50, the lumen 110 of the braided catheter tube 18, and the proximal end of the braided catheter tube 18. The proximal portion of the high pressure tube 71 extends distally from the ferrule 66 through the high pressure connection branch passageway 62, through the elongated slot 82 of the insert 50 while traversing the distal portion of the central passageway 80 en route to and into the lumen 110 of the braided catheter tube 18, and thence along the lumen 110 and into the lumen 112 of the smooth catheter tube 20 to terminate as part of the fluid jet emanator 116 shown adjacent to the flexible tapered tip 26 at the distal end of the smooth catheter tube 20. In addition to providing a passage for the high pressure tube 71, the elongated slot 82 allows communication between the lumen 110 of the braided catheter tube 18 and the lumen 112 of the smooth catheter tube 20, collectively, and the high pressure connection branch passageway 62 and the exhaust branch passageway 72 for evacuation of effluence therefrom. Also shown is the junction 118 between the smooth catheter tube 20 and the braided catheter tube 18, such junction being suitably effected to provide for a smooth and continuous coupling of the smooth catheter tube 20 and the braided catheter tube 18.

Figure 6:
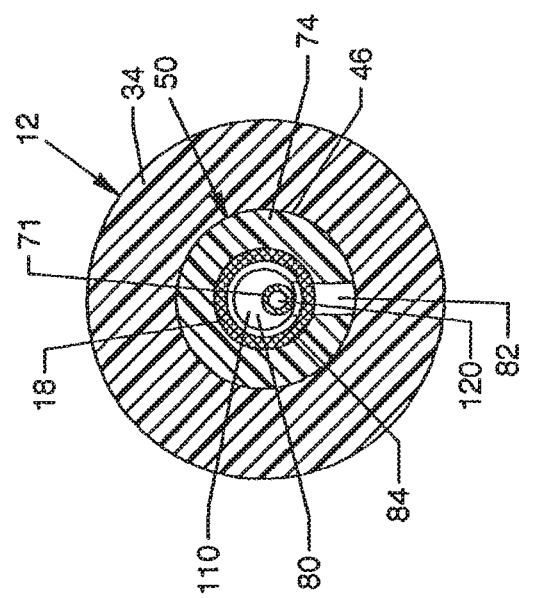
FIG. 6 is a cross section view of the thrombectomy catheter along line 6-6 of FIG. 5.

FIG. 6 is a cross section view of the enhanced cross stream mechanical thrombectomy catheter with backloading manifold 12 along line 6-6 of FIG. 5. Shown in particular is the elongated slot 82 through which the high pressure tube 71 passes (passage of high pressure tube 71 not shown) and through which communication takes place between the lumen 110 of the braided catheter tube 18 and the high pressure connection branch passageway 62 and the exhaust branch passageway 72. Also shown is a lumen 120 central to the high pressure tube 71.

Figure 7:
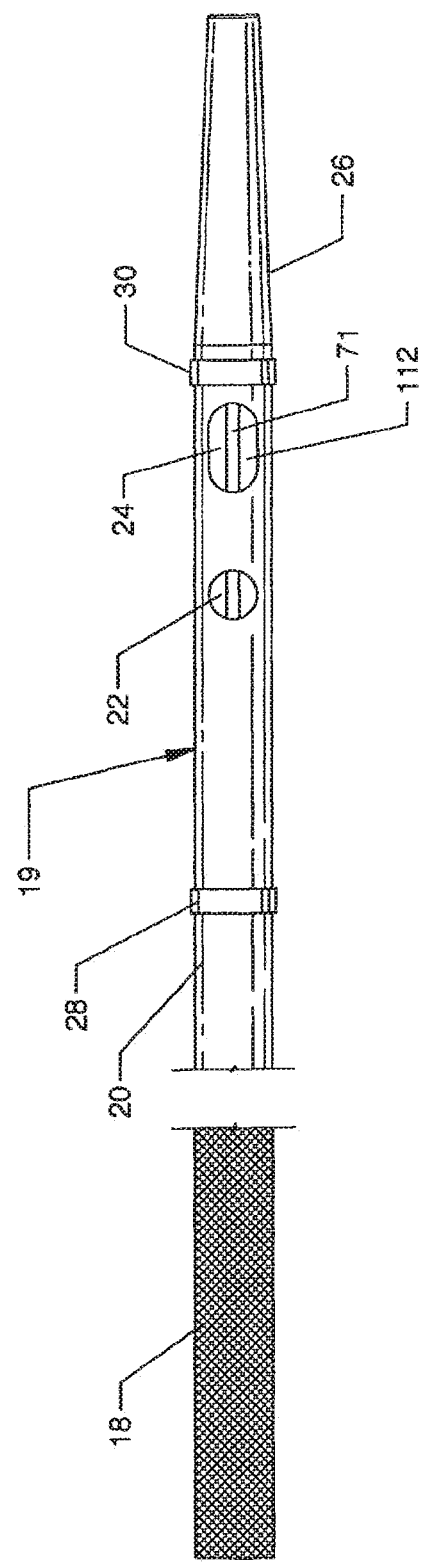
FIG. 7 is a bottom view of the distal end of the thrombectomy catheter.

FIG. 7 illustrates the distal end of the enhanced cross stream mechanical thrombectomy catheter with backloading manifold 12 showing the smooth catheter tube 20 and the outflow orifice 22 and the inflow orifice 24, as well as the high pressure tube 71 visible through the outflow orifice 22 and the inflow orifice 24.

Figure 8:
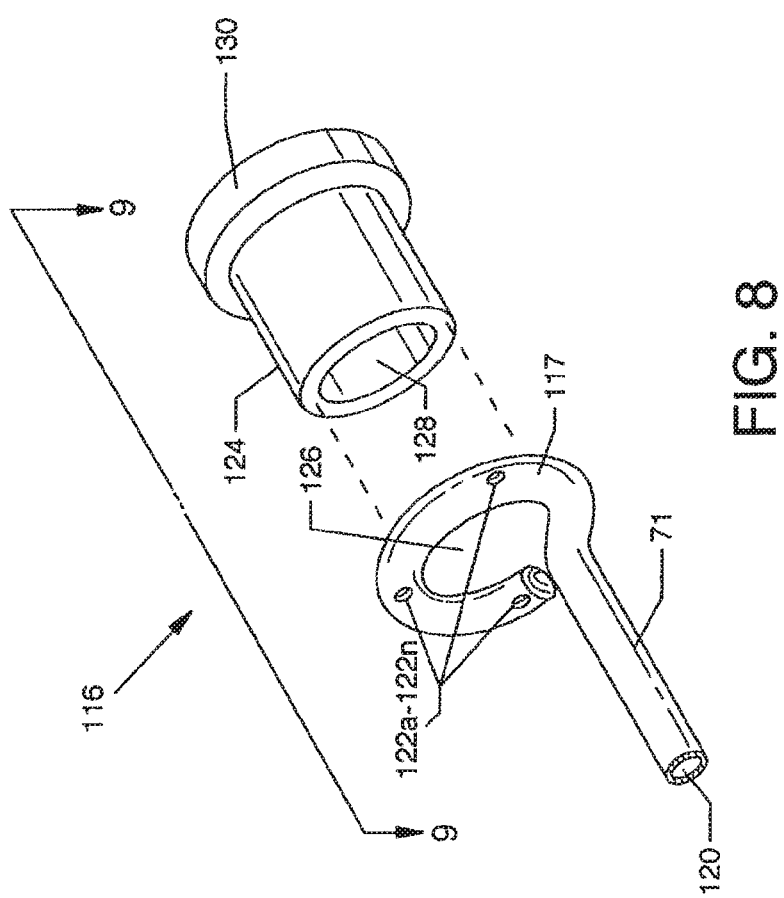
FIG. 8 is an exploded isometric view of the fluid jet emanator.
Figure 9:
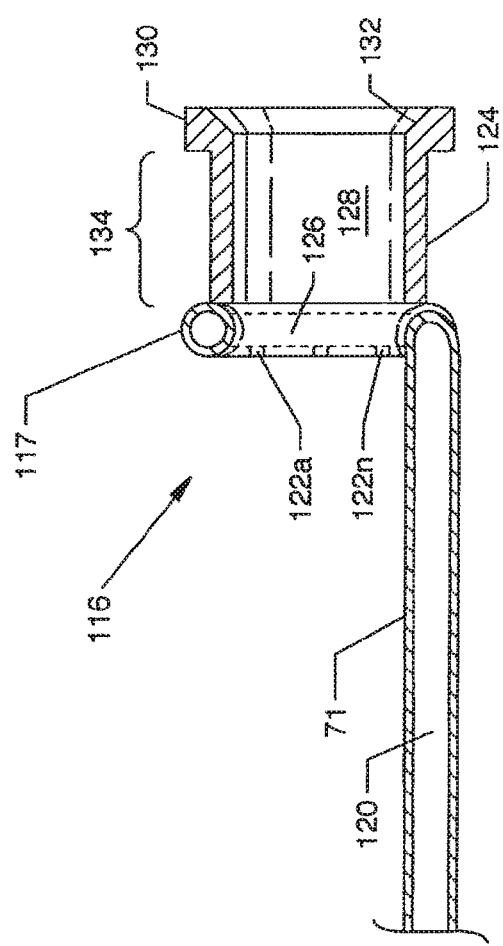
FIG. 9 is an assembled side view in cross section along line 9-9 of FIG. 8 of the fluid jet emanator.
Figure 10:
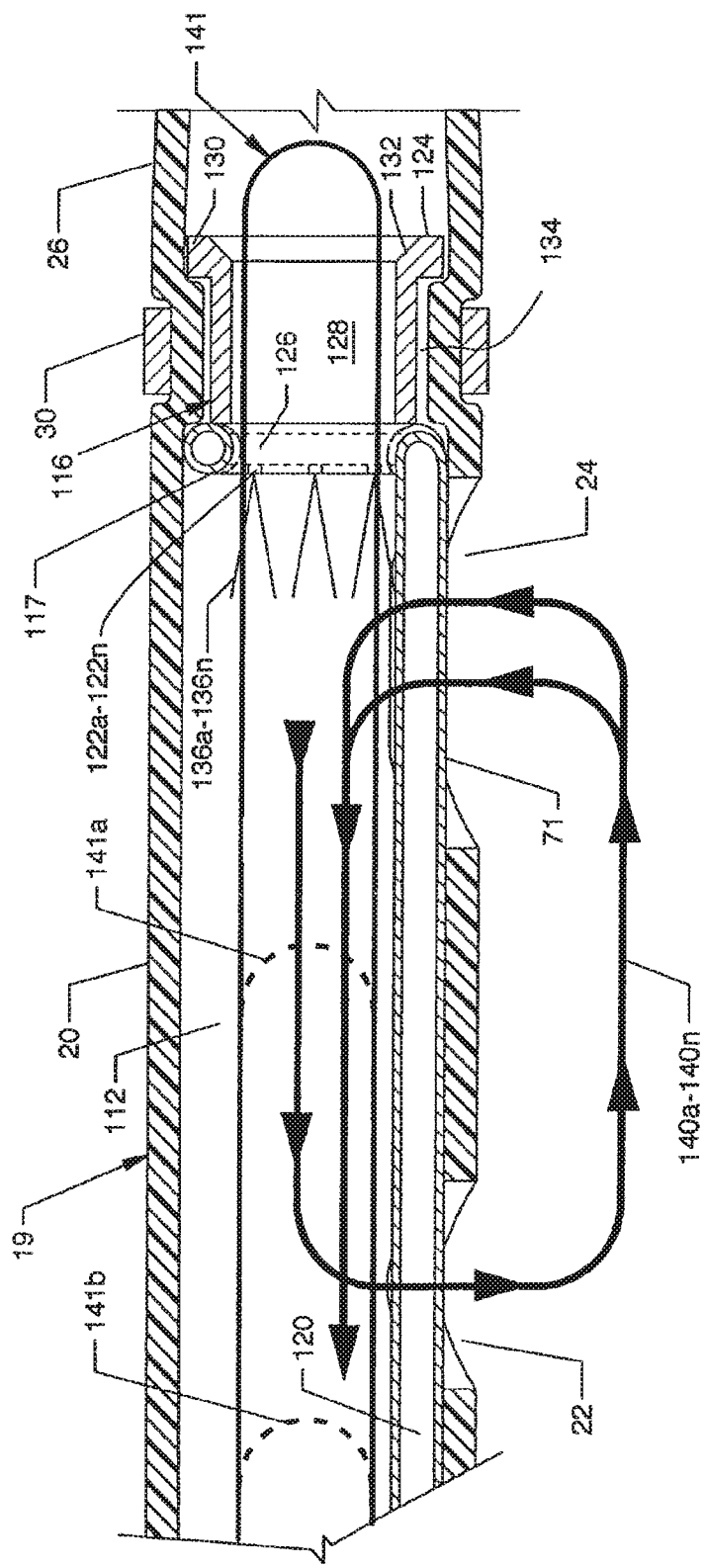
FIG. 10 is a side view in cross section illustrating the elements of FIG. 9 secured in the distal portion of the smooth catheter tube by a radiopaque marker band, as well as showing the cross stream flow.

FIG. 8 is an exploded isometric view and FIG. 9 is an assembled side view in cross section along line 9-9 of FIG. 8 of the fluid jet emanator 116. The fluid jet emanator 116 includes a terminated loop 117 at the distal end of the high pressure tube 71 and includes the support ring 124. The terminated loop 117 includes a plurality of proximally directed jet orifices 122a-122n (collectively, 122). The support ring 124 suitably secures to the distal surface of the terminated loop 117 such as by a weldment. A center void 126 of the terminated loop 117 allows for passage of a guidewire or other suitable devices. The support ring 124, a tubular device, includes a central passageway 128 corresponding in use to that of the center void 126 of the terminated loop 117 for passage of a guidewire or other suitable devices. A distally located annular shoulder 130 on the support ring 124 allows for the inclusion of a beveled annular surface 132 juxtaposing the central passageway 128 to aid in the guided accommodation of a guidewire or other suitable device at the distal portion of the central passageway 128. A wide annular groove 134 is formed between the annular shoulder 130 and the distally facing surface of the terminated loop 117 and the smaller radiused body of the support ring 124. The wide annular groove 134 is utilized to secure the fluid jet emanator 116 at a suitable location in the distal portion of the smooth catheter tube 20, as shown in FIG. 10.

The mode of operation of the enhanced cross stream mechanical thrombectomy catheter with backloading manifold 12 is explained with reference to FIGS. 10, 11, and 12. FIG. 10 illustrates the elements of FIG. 9 secured in the distal portion of the smooth catheter tube 20 by the radiopaque marker band 30 which forces an annular portion of the smooth catheter tube 20 into the wide annular groove 134 formed by the support ring 124 and the terminated loop 117 of the fluid jet emanator 116. High velocity fluid jets 136a-136n (collectively, 136) are shown emanating proximally from the plurality of jet orifices 122a-122n (collectively, 122) into the lumen 112 of the smooth catheter tube 20 for subsequent creation of and culminating in cross stream jets 140a-140n (collectively, 140), as depicted by heavy lines, which flow from the outflow orifice 22 and return through the inflow orifice 24 for ablative action with thrombus material and for maceration of foreign material in concert with the high velocity fluid jets 136a-136n and/or for exhausting proximally with the flow within the distal portion of the smooth catheter tube 20. A guidewire 141 is also shown in see-through depiction, including alternate guidewire end positions 141a and 141b designated by dashed lines, where the guidewire 141 extends along the lumen 112 of the smooth catheter tube 20, through the center void 126 of the terminated loop 117, and through the central passageway 128 of the support ring 124 into the proximal portion of the flexible tapered tip 26. Guidewire 141 can be advanced beyond the flexible tapered tip 26 of the smooth catheter tube 20 such as during positioning of the catheter within the blood vessel or other body cavity, and then withdrawn to alternate guidewire end positions 141a and 141b, or other positions within the smooth catheter tube 20, or withdrawn completely from the smooth catheter tube 20. An advantage of an embodiment of the present disclosure is that the guidewire 141 can be introduced by a front loading approach or by a backloading approach and, therefore, can be removed and reintroduced or can be replaced by a different guidewire.

Figure 11:
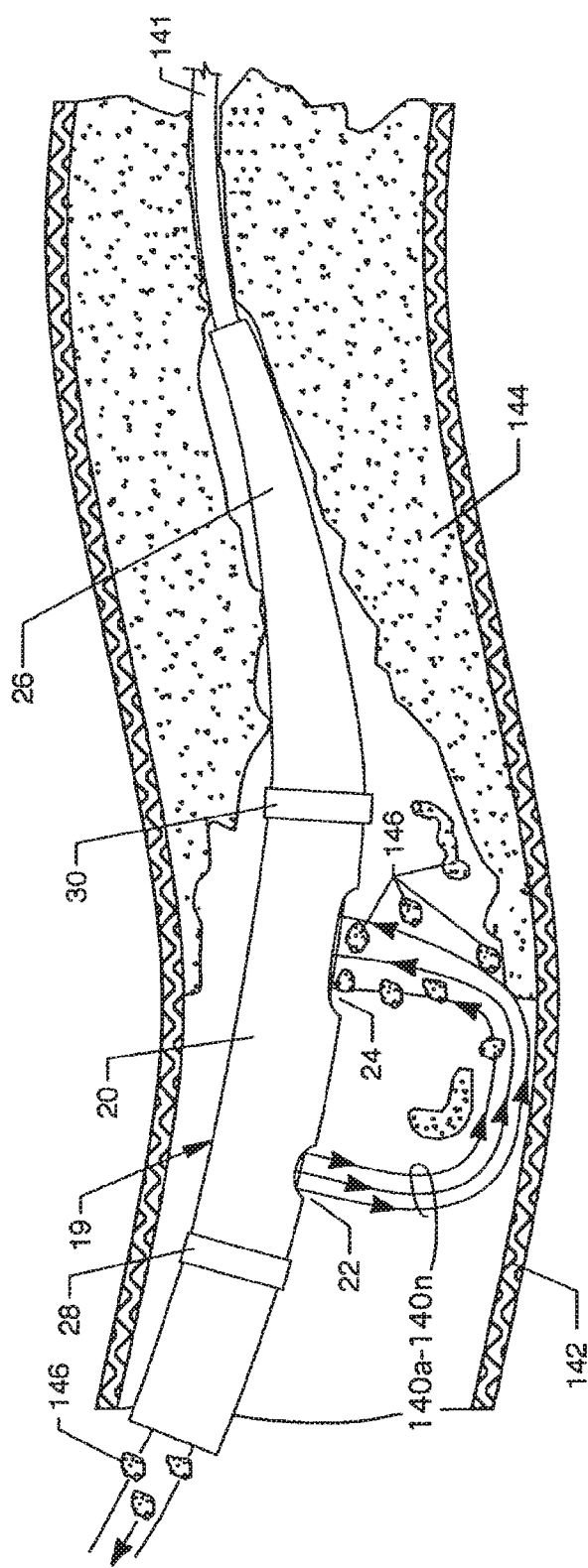
FIG. 11 is a side view of the distal region of the thrombectomy catheter showing the distal end of a smooth catheter tube assembly positioned in a blood vessel (shown in cross section) at a site of a thrombotic deposit or lesion.

FIG. 11 is a side view of the distal region of the enhanced cross stream mechanical thrombectomy catheter with a backloading manifold 12 showing in particular the distal end of the smooth catheter tube assembly 19 positioned in a blood vessel 142 (shown in cross section) at a site of a thrombotic deposit or lesion 144. While FIG. 11 depicts the smooth catheter tube assembly 19 as being in a blood vessel in particular, it is to be understood that it is not limited to use in a blood vessel but has utility with respect to any body cavity in general. High velocity fluid jets 136a-136n (shown in FIG. 10) of saline or other suitable solution are emanated or emitted in a proximal direction from the fluid jet emanator 116 into the smooth catheter tube 20 and pass through the outflow orifice 22 creating cross stream jets 140a-140n directed toward the wall of the blood vessel 142 having thrombotic deposits or lesions 144 and thence are influenced by the low pressure at the inflow orifice 24 to cause the cross stream jets 140a-140n to be directed distally substantially parallel to the central axis of the blood vessel 142 to impinge and break up thrombotic deposits or lesions 144 and to, by entrainment, urge and carry along the dislodged and ablated thrombotic particulates 146 of the thrombotic deposits or lesions 144 through the inflow orifice 24, a relatively low pressure region, and into the lumen 112, which functions as a recycling maceration lumen or chamber and also as an exhaust lumen. The entrainment through the inflow orifice 24 is based on entrainment by the high velocity fluid jets 136a-136n. The outflow is driven by internal pressure which is created by the high velocity fluid jets 136a-136n and the fluid entrained through the inflow orifice 24. The enhanced clot removal is enabled because of the recirculation pattern established between inflow orifice 24 and outflow orifice 22, which creates a flow field that maximizes drag force on wall-adhered thrombus, and because of impingement of the cross stream jets 140a-140n. The cross stream jets 140a-140n, whilst being forcefully directed outwardly and toward the wall of the blood vessel 142, by opposite reaction urge the distal portion of the smooth catheter tube 20 in the direction opposite the outward flow direction and away from the impingement area of the cross stream jets 140a-140n with the immediate thrombotic deposit or lesion 144 and/or the wall of the blood vessel 142, thus distancing the highly concentrated high velocity cross stream jets 140a-140n from the immediate thrombotic deposit or lesion 144 and/or the wall of the blood vessel 142 and thereby minimizing potential blood vessel wall damage. The cross stream jets 140a-

140n traversing between the outflow orifice 22 and the inflow orifice 24 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 140a-140n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 20 can be rotated axially to direct the cross stream jets 140a-140n about a longitudinal axis to have 360° coverage or can be rotated axially to offer coverage partially about the longitudinal axis, as required.

The placement of the guidewire 141 within or the removal of the guidewire 141 from the enhanced cross stream mechanical thrombectomy catheter with backloading manifold 12 influences the operation of an embodiment of the present disclosure. Suitably strong and well directed ablation flow can take place with a guidewire 141 extending the full length of the enhanced cross stream mechanical thrombectomy catheter with backloading manifold 12 and/or additionally extending in a distal direction beyond the flexible tapered tip 26 and along the vasculature. Such ablation flow can be further improved, enhanced, modified or otherwise influenced by varying the location of or by full removal of the guidewire 141. With reference to FIG. 10, the guidewire 141, as shown, allows suitable transition of the high velocity fluid jets 136a-136n through the outflow orifice 22 to form cross stream jets 140a-140n which return via the inflow orifice 24. If, for example, the guidewire 141 is urged proximally to a guidewire end position 141a between the inflow orifice 24 and the outflow orifice 22, the inflow orifice 24 is totally unrestricted and has less flow resistance, thereby allowing greater and more forceful ingress of the cross stream jets 140a-140n laden with ablated thrombotic particulates 146, whereas the flow through the outflow orifice 22 remains substantially constant. Urging the guidewire 141 further in a proximal direction to a guidewire end position 141b distal to the outflow orifice 22 causes the outflow orifice 22 and the inflow orifice 24 both to be totally unrestricted and both to have less flow resistance, thereby allowing greater and more forceful flow from the outflow orifice 22, as well as resultantly increased ingress of the cross stream jets 140a-140n laden with ablated thrombotic particulates 146 through the inflow orifice 24. Each of the examples given herein where the guidewire 141 is not totally removed from the smooth catheter tube 20 or other proximally located regions promotes sustained maceration of the loitering entrained ablated thrombotic particulates 146 where the smaller ablated thrombotic particulates 146 are exhausted proximally through the smooth catheter tube 20, the braided catheter tube 18, and the associated and pertinent structure proximal thereto. In another example, urging of the guidewire 141 to a position proximal of the proximal end of the braided catheter tube 18 or total removal of the guidewire 141, in addition to allowing total unrestricted flow through the outflow orifice 22 and the inflow orifice 24, allows unrestricted flow of ablated thrombotic particulates 146 along the smooth catheter tube 20, the braided catheter tube 18, and the associated and pertinent structure proximal thereto.

Although the illustrated cross stream mechanical thrombectomy catheter incorporates an inflow orifice 24 and an outflow orifice 22 aligned to the high pressure tube 71, one or both of the inflow or outflow orifices may be located so that they do not align with the high pressure tube; in this case, other means for guiding a guidewire past the orifice(s) is provided to prevent the guidewire from inadvertently passing through the non-aligned orifice(s).

Figure 12:
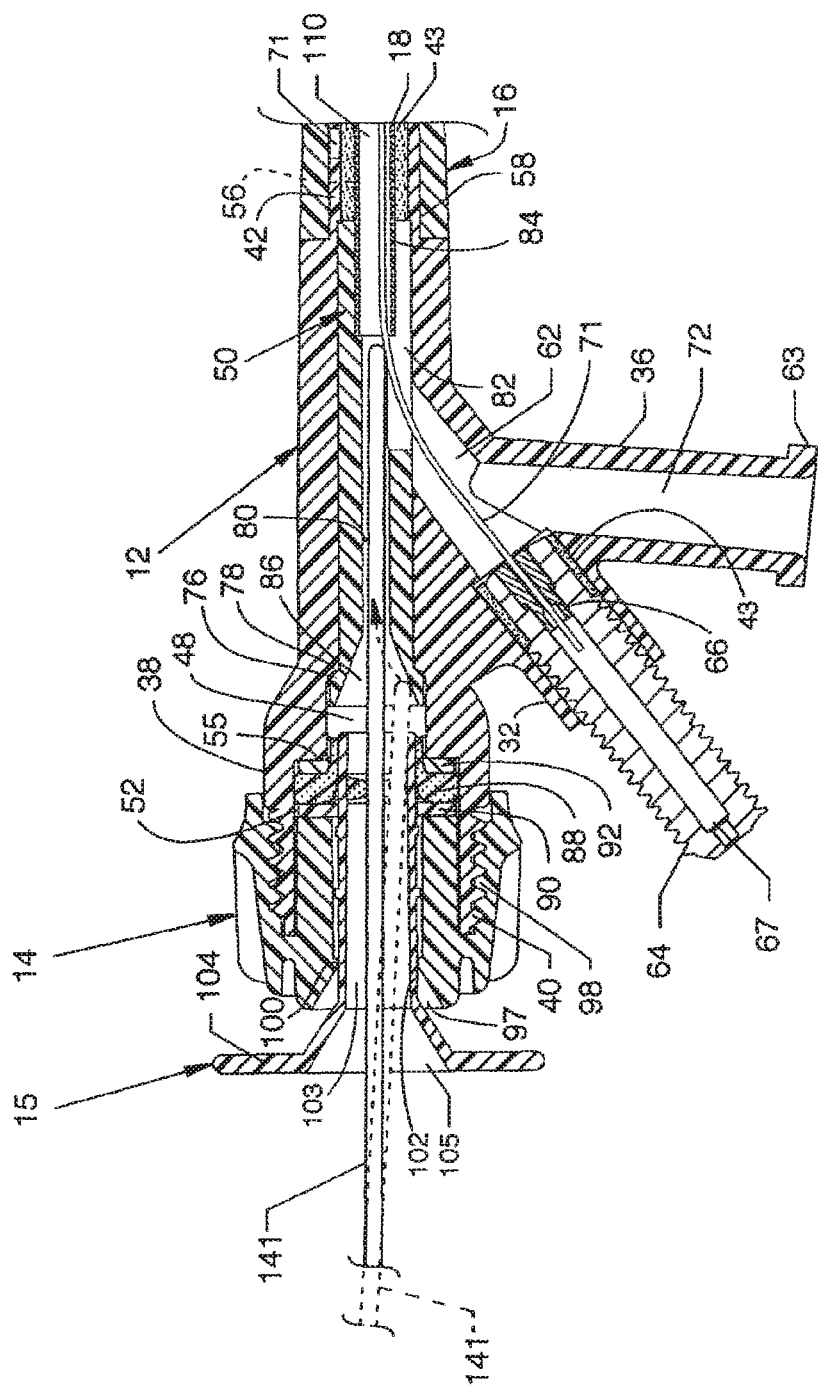
FIG. 12 is a side view in cross section illustrating the introduction of a guidewire into the thrombectomy catheter.

FIG. 12 is a side view in cross section illustrating the introduction of the guidewire 141 into the enhanced cross stream mechanical thrombectomy catheter with backloading manifold 12. When it is desired to remove a guidewire, such as guidewire 141, or exchange guidewires having different attributes, backloading is facilitated by the structure of the insert 50. Loading can be accomplished, if necessary, using the introducer 15 to gain entry through the self-sealing hemostatic valve 88 where the introducer parts the sealing structure of the self-sealing hemostatic valve 88 to allow entry of the guidewire 141 therethrough. Otherwise the guidewire can pass unaided through the self-sealing hemostatic valve 88. The tip of the guidewire may not be in proper alignment with the central passageway 80, such as is shown by the guidewire 141 shown in dashed lines. In such case, impingement of the tip of the distally urged guidewire 141 with the conically-shaped beveled surface entrance 86 of central passageway 80 directs the tip of the guidewire 141 to align with and to be engaged within the central passageway 80 of the insert 50 and to be in alignment, as shown, within the central passageway 80 so as to align with and be subsequently engaged within the proximal portion of the braided catheter tube 18 for passage therethrough. Distal urging of the guidewire 141 also positions the tip of the guidewire 141 for passage through the distal region of the smooth catheter tube 20 where the geometry helpfully accommodates such passage by and along the outflow orifice 22 and the inflow orifice 24 and through the fluid jet emanator 116, the support ring 124, and the flexible tapered tip 26. Preferably, the tip of the guidewire 141 is dome-shaped. Such a dome shape is easily guided by and accommodated by the proximally-facing rounded surface of the terminated loop 117 of the fluid jet emanator 116. Use of the introducer 15 can also be utilized if front loading of a guidewire is required for passage through the self-sealing hemostatic valve 88. Preferably, the guidewire 141 exhibits sufficient size, flexibility and other attributes to navigate the tortuous vascular paths, but exhibits sufficient rigidity not to kink, bend or otherwise be permanently deformed and to stay within the appropriate confines of the distal portion of the smooth catheter tube 20 and not stray through the outflow orifice 22 or the inflow orifice 24. The cross sections of the outflow orifice 22 and the inflow orifice 24 are such that entry thereinto of the horizontally aligned guidewire of sufficient size and larger cross section profile is next to impossible. Notwithstanding, the use of one pair of inflow and outflow orifices further reduces the chance of inadvertent exiting of the guidewire tip through an orifice. This is just one illustrative thrombectomy catheter. Other thrombectomy catheters are described in commonly assigned U.S. Pat. Nos. 8,998,843 and 9,078,691, which are herein incorporated by reference.

Figure 13:
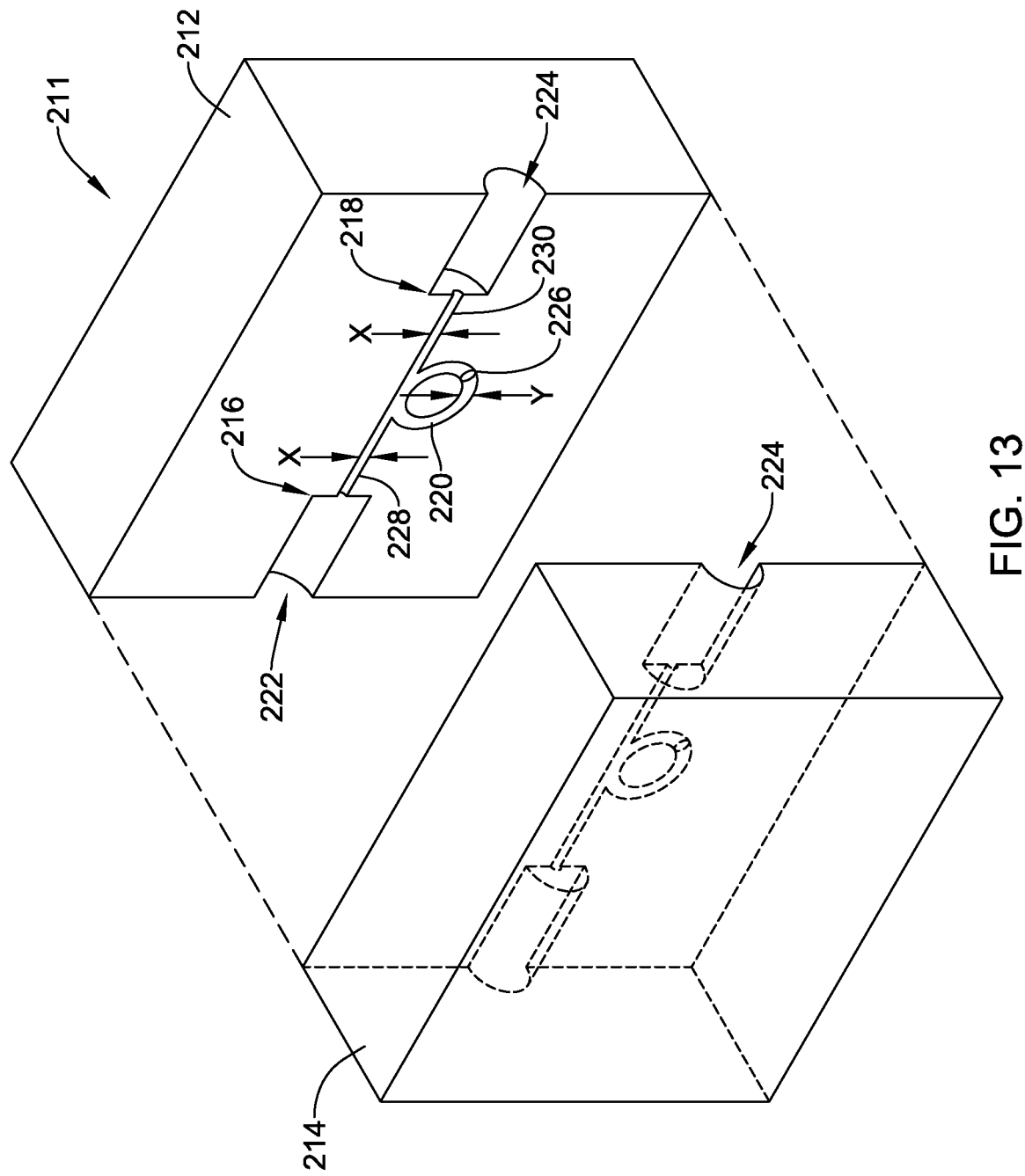
FIG. 13 is an exploded view of an example fluid pulse generator.

FIG. 13 illustrates an exploded view of example pulse generator 211. Pulse generator 211 may include a first block portion 214 coupled to a second block portion 212. Together, block portion 212 and block portion 214 may form a fluid inlet portion 216, a fluid outlet portion 218 and a frequency modulating portion 220 extending therein. It can be appreciated that an external fluid source may be coupled to fluid inlet portion 216 at attachment portion 222. This external fluid source may inject fluid into pulse generator 211. As described above, the fluid may be injected into pulse generator 211 at a constant flow rate. It can further be appreciated that after injected fluid passes through fluid inlet portion 216, it may travel through frequency modulating portion 220 before exiting (e.g., being ejected out of) pulse generator 211 via fluid outlet portion 218.

As shown in FIG. 13, both fluid inlet portion 216 and fluid outlet portion 218 may include an inlet lumen 228 and exit lumen 230 each having a diameter "X." Additionally, FIG. 13 illustrates that frequency modulating portion 220 may include a diameter "Y." In at least some examples, diameter "Y" is larger than diameter "X." Further, FIG. 13 illustrates that frequency modulating portion 220 may include a disrupter 226. However, this is not intended to be limiting. Rather, disrupter 226 may include a variety of geometric shapes. In some examples, disrupter 226 may be a spherical member (e.g., a spherical ball). Additionally, disrupter 226 may be constructed from a variety of materials such as a metal, a polymer or combinations thereof.

Once fluid is passed through inlet portion 216 it may flow around frequency modulating portion 220. In at least some instances, it can be appreciated that as fluid flows around frequency modulating portion 220, disrupter 226 may engage (e.g., contact) the fluid passing between the inlet portion 216 and outlet portion 218. This interaction of disrupter 226 with the fluid flow may disrupt the constant flow rate of fluid entering pulse generator 211. This disruption may transform the fluid flowing through the pulse generator from a constant flow rate to the pulsatile flow rate described above. Further, this pulsatile flow may occur at a particular frequency and at a particular power. It can be appreciated that the frequency at which the pulsatile flow rate occurs may be dependent on the size of disrupter 226 and/or the diameter "Y" of frequency modulating portion 220 and/or lumen 228 and/or lumen 230.

Additionally, it can be appreciated that pulse generator 211 may be attached to example thrombectomy catheters via attachment portion 224. Further, as described above, pulse generator 211 may be designed such that the fluid exiting pulse generator 211 may approximate and/or match a resonant frequency of the thrombus, plaque, etc. being targeted in a given procedure. For example, approximating a resonant frequency may include identifying a frequency within a given range around the resonant frequency. For example, pulse generator 211 may be designed such that fluid exiting pulse generator 211 may be with 0-5% of the resonant frequency, or within 5-15% of the resonant frequency, or within 15-25% of the resonant frequency, for example.

The example pulse generator 11 described above may include example pulse generator 211. However, this is not intended to be limiting. Pulse generator 11 may also include other examples which create pulsatile flow at a selected frequency (e.g., at the resonant frequency of targeted thrombus, plaque, etc.) and a given power. Other pulse generators may utilize ultrasound energy, other forms of mechanical energy/disrupters, electrical energy/disrupters, piezo-electric pulses, or the like. For example, in addition to the "reciprocating ball" generator described above with respect to FIG. 13, other pulse generators may include an oscillating reed generator, a mechanical toggle, piezo-electric generators, servo-generated pulse generators, etc. Additionally, combinations of any of the pulse generators described here are contemplated.

While the foregoing discussion describes that pulse generator 11 or other pulse generators contemplated herein may be utilized with catheter system 10, it can also be appreciated that any of the pulse generators described here may be used with other thrombectomy systems or methods. For example, pulse generators described herein may be coupled to a catheter shaft and/or tubular member having a lumen extending therein. Additionally, the pulse generators described herein may be coupled to a catheter shaft and/or tubular member having one or more orifices extending therein. This may include the use of pulse generator 11 with a number of different thrombectomy systems or devices. The pulse generators described herein may be utilized with a guidewire or other accessory device. For example, pulse generators described herein may be utilized with fluid delivery devices. Further, the pulse generators described herein may include a particular device tip that generates pulsatile flow.

The materials that can be used for the various components of the catheters, guidewires, accessory device, and/or other devices disclosed herein may include those commonly associated with medical devices. For simplicity purposes, the following discussion makes reference to thrombectomy systems and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the thrombectomy systems and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the thrombectomy devices and their related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A thrombectomy catheter, comprising:
   a catheter tube including a proximal portion, a distal portion, and a lumen extending therein;
   a high pressure tube extending through the catheter lumen from the catheter proximal portion toward the catheter distal portion, the high pressure tube having at least one jet orifice for directing at least one fluid jet through the catheter lumen;
   an outflow orifice;
   an inflow orifice; and
   a fluid pulse generator coupled to the proximal portion of the catheter tube;
   wherein the fluid pulse generator is configured to receive a fluid flow and modify the received fluid flow into a pulsed fluid flowing through the thrombectomy catheter at a first frequency;
   wherein the first frequency is 20-30 MHz.

2. The thrombectomy catheter of claim 1, wherein the first frequency approximates a resonant frequency of a target site.

3. The thrombectomy catheter of claim 1, wherein the fluid pulse generator is configured to receive the fluid flow at a second frequency different from the first frequency.

4. The thrombectomy catheter of claim 1, wherein the first frequency is within 5% of the resonant frequency.

5. The thrombectomy catheter of claim 1, wherein the first frequency is less than or equal to 30 MHz.

6. The thrombectomy catheter of claim 1, wherein the first frequency is 23-27 MHz.

7. The thrombectomy catheter of claim 1, wherein the fluid pulse generator includes a fluid inlet portion, a fluid outlet portion, and a frequency modulating portion extending therebetween.

8. The thrombectomy catheter of claim 7, wherein the frequency modulating portion includes a disruptor, and wherein the disruptor is intended to disrupt the flow of fluid through the fluid pulse generator.

9. A thrombectomy catheter, comprising:
   a catheter tube including an inlet portion, an outlet portion, and a lumen extending therein; and
   a fluid pulse generator coupled to the inlet portion of the catheter tube;
   wherein the fluid pulse generator is configured to receive a fluid flow and modify the received fluid flow into a pulsed fluid flowing through the lumen of the catheter tube at a first frequency of 20-30 MHz.

10. The thrombectomy catheter of claim 9, wherein the first frequency approximates a resonant frequency of a target site.

11. The thrombectomy catheter of claim 9, wherein the fluid pulse generator is configured to receive the fluid flow at a second frequency different from the first frequency.

12. The thrombectomy catheter of claim 9, wherein the first frequency is 23-27 MHz.

13. The thrombectomy catheter of claim 9, wherein the fluid pulse generator includes a fluid inlet portion, a fluid outlet portion, and a frequency modulating portion extending therebetween.

14. The thrombectomy catheter of claim 13, wherein the frequency modulating portion includes a disruptor, and wherein the disruptor is intended to disrupt the flow of fluid through the fluid pulse generator.

* * * * *